(12) United States Patent
Harmstorf

(10) Patent No.: US 6,760,102 B2
(45) Date of Patent: Jul. 6, 2004

(54) METHOD AND APPARATUS FOR CONTINUOUS DETECTION AND LOCALIZATION OF YARN DEFECTS IN A YARN SHEET TRAVELING IN A PLANE

(75) Inventor: Jens Harmstorf, Bobingen (DE)

(73) Assignee: Arteva Technologies, S.a.r.l., Zurich (CH)

( * ) Notice: Subject to any disclaimer, the term of this patent is extended or adjusted under 35 U.S.C. 154(b) by 0 days.

(21) Appl. No.: 10/313,356

(22) Filed: Dec. 6, 2002

(65) Prior Publication Data
US 2003/0112429 A1 Jun. 19, 2003

(30) Foreign Application Priority Data
Dec. 14, 2001 (DE) .......................... 101 61 502

(51) Int. Cl.$^7$ .............................................. G01N 21/00
(52) U.S. Cl. .................................. 356/238.1; 356/238.2
(58) Field of Search ........................ 356/238.1–238.2; 250/559.01–559.18, 219; 382/111

(56) References Cited

U.S. PATENT DOCUMENTS

| | | | |
|---|---|---|---|
| 3,717,771 A | * | 2/1973 | Abilock et al. ........ 250/559.03 |
| 3,765,777 A | * | 10/1973 | Williams, Jr. ................ 356/430 |
| 4,901,519 A | | 2/1990 | Wassenhoven et al. |
| 4,934,814 A | | 6/1990 | Scholz |
| 5,414,520 A | | 5/1995 | Joss et al. |
| 5,420,439 A | | 5/1995 | Landwehrkamp et al. |
| 5,684,598 A | | 11/1997 | Harke et al. |
| 6,369,896 B1 | * | 4/2002 | Castello et al. ............. 356/430 |

FOREIGN PATENT DOCUMENTS

DE  A 29 33 297  8/1979

* cited by examiner

Primary Examiner—Michael P. Stafira
(74) Attorney, Agent, or Firm—Gregory N. Clements

(57) ABSTRACT

To detect yarn defects such as protruding filaments, broken filaments, ringers, fuzzballs, stripbacks and the like, a yarn sheet 9 traveling in a plane is scanned by light beams from at least two light barriers 10, 11. When a yarn defect interrupts the light beam of a light barrier, a detector pulse is triggered, appropriately amplified and transformed and sent to evaluating means 22. Such a detector pulse is triggered each time a yarn defect passes through a light barrier, so that the travel time or time difference $T_{1,2}$ between the trip times of a yarn defect through the two light barriers can be determined by the evaluating means. Since the yarn sheet 9 passes through the light barriers at a constant velocity v, the travel times for the various individual ends from one light barrier to the next will differ and therefore can be used to determine the distance S normal to the yarn traveling direction of the yarn defect to the point of intersection of the light beams of the two light barriers. When one of the light beams is oriented perpendicularly to the yarn traveling direction, the equation $S = T_{1,2} * v / \tan \alpha$ applies. The light barriers 10, 11, which each comprise a light source and a detector, are arranged relative to each other in a V-shape and their light beams form the angle $\alpha$.

31 Claims, 5 Drawing Sheets

METHOD AND APPARATUS FOR CONTINUOUS DETECTION AND LOCALIZATION OF YARN DEFECTS IN A YARN SHEET TRAVELING IN A PLANE

BACKGROUND OF THE INVENTION

1) Field of the Invention

This invention relates to a method and apparatus for continuous detection and localization of yarn defects in a yarn sheet which is traveling in a plane and which is scanned by light beams for yarn defects such as protruding filaments, broken filaments, fuzzballs, stripbacks, ringers and the like, each light beam interruption triggered by such a yarn defect, thereby triggering a detector pulse.

2) Prior Art

The monitoring of traveling yarns for diameter fluctuations and particularly for protruding filaments, yarn defects, i.e. broken filaments, fuzzballs, ringers, stripbacks and the like, in the production of yarns in the manufactured fiber or textile industry using optical detector devices such as for example light barriers is known.

Such a device for monitoring a single traveling thread or yarn for diameter fluctuations and protruding filaments using a light barrier operating in the infrared region is described in DE 29 33 297 A.

Similar light barriers are used to monitor sheets of some hundred unwinding yarns in the production of warp beams. With this procedure, only relatively coarse yarn defects and broken yarn are identified as defects; these light barriers are unable to recognize broken individual filaments in individual yarns. Localization of the yarn defect at right angles to the yarn direction is generally only possible at huge cost and inconvenience, if at all.

EP 0 296 469 B1 discloses a process for determining quality characteristics of traveling yarns by using defect counters to determine the number of yarn irregularities. The yarn passes through at least three successive defect sensors of the same type whose counting pulses emitted on passage of a yarn section of the freely chosen length L are converted into a length-based average R by disregarding from the averaging any greatly deviant individual measurements as spurious values. The apparatus used to carry out the process consists of at least three defect sensors disposed consecutively in the yarn path, means for measuring the traversing yarn length L and an arithmetic processing unit which sums the counting pulses separately for each sensor to form pulse totals and stores these pulse total values. The totals obtained are tested for spurious values according to predetermined criteria and such values are eliminated. Useful means for measuring the yarn length include any arrangement known for this purpose, for example a measuring roller of a certain circumference which is rotated without slippage by the traveling yarn and whose number of revolutions is recorded. To monitor a sheet of yarn, every individual yarn has to be inspected by such apparatus; the cost is accordingly enormous.

DE 195 26 646 A1 discloses a process for monitoring a traveling yarn sheet by passing the yarn sheet over guide bars upstream and downstream of the monitoring site and sending at least one light beam at right angles to the traveling direction of the yarn sheet and parallel to the yarn sheet plane to photoreceptors. The signals from the photoreceptors are evaluated by an electronic evaluating unit and recorded. At least four photoreceptors are used, of which at least two are disposed successively in the yarn traveling direction and at least two above each other in such a way that there is at least one photoreceptor below and at least one photoreceptor above the yarn sheet plane. All the photoreceptors are disposed in such a way that they form superposed pairs and all the pairs are disposed one behind the other. This known apparatus preferably employs 4 quadrant photoreceptors or multisegmental photocells. The monitoring arrangement is formed by a light source, which can be a laser light source, a lens for parallelizing the light beam, a diaphragm for determining the light beam cross section, a further diaphragm for intercepting stray rays, a lens for focusing light beams and a 4 quadrant photoreceptor or a multisegmental photocell. The technical complexity of this apparatus is enormous. A specific method for localizing a yarn defect at right angles to the yarn direction is not described.

DE 38 32 984 C2 discloses a process and apparatus for indicating broken ends in a yarn sheet traveling in a plane by scanning the yarn sheet with a laser beam at right angles to the traveling direction of the yarn sheet in continually repeated passes and counting the light pulses reflected by the individual ends per passage by means of detectors. The number of light pulses is compared with a target value for the number of individual ends and deviations from the target value are indicated. For this, a multiplicity of detectors are disposed side by side substantially equal distances apart in a row which is perpendicular to the yarn traveling direction and in a plane which is parallel to the yarn sheet plane, in such a way that reception areas overlap. The detectors are oriented in an identical angle, the backbeam angle, to the line of incidence of a laser beam reflected by a rotating mirror, with the yarn sheet. The laser beam is disposed relative to the yarn sheet and relative to the row of detectors in such a way that the angle of incidence of the laser beam reflected by the rotating mirror on the yarn sheet and the backbeam angle are substantially the same. At least three and preferably at least five passes are grouped together in a cycle and the light pulses are counted per pass and compared with the predetermined target value for the number of individual ends. Absent agreement between the two values, a defect signal is generated and counted in a counter. At the end of each cycle, the final value of the counter is compared with a predetermined limiting value and when the limiting value is reached or exceeded the yarn sheet is stopped. Again, the technical complexity of this process and apparatus is comparatively large.

WO93/06466 describes a process for detecting and counting yarn defects in a yarn segment using a camera, a computer and an image processing program. The yarn is recorded by the camera with an intensity which depends on the thickness of the yarn. The recorded image is digitized in the computer by the image processing program and low-contrast points are filtered out. The points which remain are grouped together into continuous areas whose size is categorized into predetermined size classes and stored. The process makes it possible to count yarn defects, for example. yarn impurities, objectively and reproducibly. This process is not intended for inspecting a fast-traveling yarn sheet for defects in individual ends.

WO93/19359 discloses a process and apparatus for detecting impurities in a textile test material. For this, the test material is illuminated for at least two locations and the light reflected by the test material is measured by receptors and in addition to the reflection the diameter or diameter changes of the test material are measured. The measured signals obtained are combined and the resulting signal is examined for deviations from a predetermined value. If a deviation is ascertained, an impurity is present in the test material. The checking of a fast-traveling yarn sheet for yarn defects is not possible by this process and the apparatus intended for it.

It is also known for a yarn sheet to be monitored using commercially available single light barriers and to be stopped in the event of a yarn defect occurring. In this process, the operating personnel subsequently has to search for the yarn defect and to cut it out, for example, and subsequently to piece the yarn back together by means of a knot. The only information to guide the search for the yarn defect that the operating personnel has available is that the position of the yarn defect is localized in the yarn traveling direction. This position follows from the original traveling speed of the yarn sheet and the speed deceleration to stopping by the brakes which stop the yarn sheet. There is no information about the position of the yarn defect at right angles to the traveling direction of the yarn sheet, so that the operating personnel has to scour the entire width of the yarn sheet, which can be up to about 300 cm, to find the yarn defect.

SUMMARY OF THE INVENTION

It is an object of the present invention to design a process and apparatus at minimal cost and inconvenience in such a way that the position of a yarn defect in a traveling yarn sheet at right angles to the traveling direction is quicker to find than in existing processes and apparatus.

This object is achieved according to the invention by the yarn sheet passing through a measuring arrangement which comprises light barriers which are made up of light sources and detectors being arranged relative to each other in a V-shape and also evaluating means, the light beams of the light barriers extending parallel to the yarn sheet plane, at constant speed and the travel distances of the individual ends from one light barrier to the next differing in length.

Since all ends of the yarn sheet have the same velocity, the difference in travel length gives rise to a time difference between the light barriers responding. This time difference is a measure of the position of the yarn defect at right angles to the traveling direction of the yarn sheet. The position of the yarn defect in the traveling direction of the yarn sheet (stop position) is, as described above, defined by the fact that at least one of the light barrier signals is also used to stop the yarn sheet.

In carrying out the invention, the light beams of two adjacent light barriers which are disposed in a V-shape either converge or diverge relative to each other from the light sources.

In further development of the invention, the time difference $T_{1,2}$ between the trip times of a yarn defect through the two light barriers in a V-shaped arrangement of two light barriers in which the light beam of one light barrier is perpendicular to the traveling direction of the yarn sheet is determined by the equation $T_{1,2} = S^*\tan(\alpha)/v$ where S is the distance which is perpendicular to the traveling direction of the yarn sheet between the point of intersection of the light beams of the two light barriers and the yarn defect, $\alpha$ is the angle between the light beams of the light barriers and v is the velocity of the yarn sheet.

The angle $\alpha$ is in the range from 5° to 85° and especially in the range from 10 to 45°.

In general development of the process, the time difference $T_{1,2}$ between the trip times of a yarn defect through the two light barriers in a V-shaped arrangement of two adjacent light barriers which are both inclined relative to the normal to the traveling direction of the yarn sheet, the first triggered light barrier including an angle $\beta$ with the normal that is positive in the counter clockwise direction and negative in the clockwise direction with regard to the point of intersection of the light beams of the two light barriers is determined as per the equation $$T_{1,2} = k^* S^* \tan \alpha / v \qquad (1)$$

where the correction factor $$k = (1+\tan^2\beta)/(1 \pm \tan \alpha^* \tan \beta) \qquad (2)$$

S is the distance perpendicular to the traveling direction of the yarn sheet between the point of intersection of the light beams of the two light barriers and the yarn defect, $\alpha$ is the angle between the light beams of the light barriers and v is the velocity of the yarn sheet. The (+) sign in the denominator of equation (2) holds for a divergent course of the light beams, and the (−) sign for a convergent course.

In apparatus for the continuous detection and localization of yarn defects in a yarn sheet traveling in a plane, comprising light barriers for detecting detector pulses triggered by fuzzballs, broken filaments, protruding filaments, stripbacks, ringers and the like yarn defects, at least two light barriers whose light beams form an angle $\alpha$ with each other are disposed at right angles to the traveling direction and immediately above or below the yarn sheet and parallel to the yarn sheet plane and each or every light barrier comprises a light source and a detector plus associated evaluating means.

In execution of the apparatus, the angle $\alpha$ between the light beams of two light barriers is in the range from 5° to 85° and especially in the range from 10 to 45°.

In further development of the apparatus, the detectors are connected via amplifiers and signal-shaping circuits to evaluating means which determines the time difference $T_{i,i+1}$, where $i=1,2,3,\ldots n-1$ from the trip times of a yarn defect from one light barrier to the next light barrier, where n is the number of light barriers.

In a further embodiment of the apparatus, there are three light barriers whose light beams have a common point of intersection and form an angle $\alpha$ between the first and the second light barrier and also an angle $\alpha'$ between the second and third light barrier that have the same magnitude.

In a similarly possible embodiment, there are four light barriers, the light beams of the first and second light barriers forming an acute angle $\alpha$, and those of the third and fourth light barriers forming an acute angle $\alpha'$. In this embodiment, the angles $\alpha$ and $\alpha'$ advantageously have the same magnitude, but they can also have different magnitudes. The angles $\alpha$ and $\alpha'$ are each in the range from 5 to 85° and especially in the range from 10° to 45°. The angles are chosen so that each individual light barrier captures or monitors the entire yarn sheet.

In execution of the invention, each or every light barrier comprises a light source and an associated detector and the detectors are connected via amplifiers and signal-shaping circuits to evaluating means in which the time differences $T_{i,j}$ where $i,j=1,2,\ldots n-1$, $i \neq j$ are determinable from the travel times of a yarn defect from one light barrier to each or every one of the other light barriers, where n is the number of light barriers. Preferably, the light sources are laser diodes. If desired, a plurality of light sources may be replaced by a single light source. This single light source generates a corresponding number of light beams in a known manner by prismatic beam splitting.

In further execution, the time difference $T_{i,i+1}$, between the trip times of a yarn defect through two adjacent light barriers i and i+1 is predetermined by the yarn velocity v and the geometry of the light barrier arrangement as a function of the distance $S_{i,i+1}$ of the point of intersection of the light beams of these two light barriers to the yarn defect normal to the yarn traveling direction and the angle $\alpha_{i,i+1}$ between the light beams as per the equation $T_{i,i+1}=k_1 * S_{i,i+1} * \tan \alpha_{i,i+1}/v$ where i=1, 2, 3, where $\alpha_{12}$, $\alpha_{23}$ and $\alpha_{34}$ are the angles between a first and second light barrier, between a second and third light barrier and between a third and fourth light barrier and $k_i$ is a correction factor which corrects for the inclination of the i-th light barrier in relation to the normal to the traveling direction of the yarn sheet.

The correction factor $k_i=(1+\tan \beta_i^2)/(1 \pm \tan \alpha_{i,i+1} * \tan \beta_i)$ where i=1, 2, 3 includes the angle $\beta_i$ which reflects the inclination of the i-th light barrier in relation to the normal to the traveling direction of the yarn sheet and the (+) sign in the denominator indicates that the adjacent light barriers diverge and the (−) sign indicates that they converge.

When all light beams have a common point of intersection or lie on a straight line which is parallel to the yarn sheet, $S_{i,i+1}=S$ will have the same magnitude for all light barrier pairs.

Owing to the limited time resolution of the measuring system, the distances $S_{i,i+1}$ or S can only be determined with a certain locational deviation LA as will be more particularly described in what follows.

BRIEF DESCRIPTION OF THE DRAWINGS

The invention will now be illustrated with reference to drawings, where.

DESCRIPTION OF THE PREFERRED EMBODIMENTS

Figure 3:
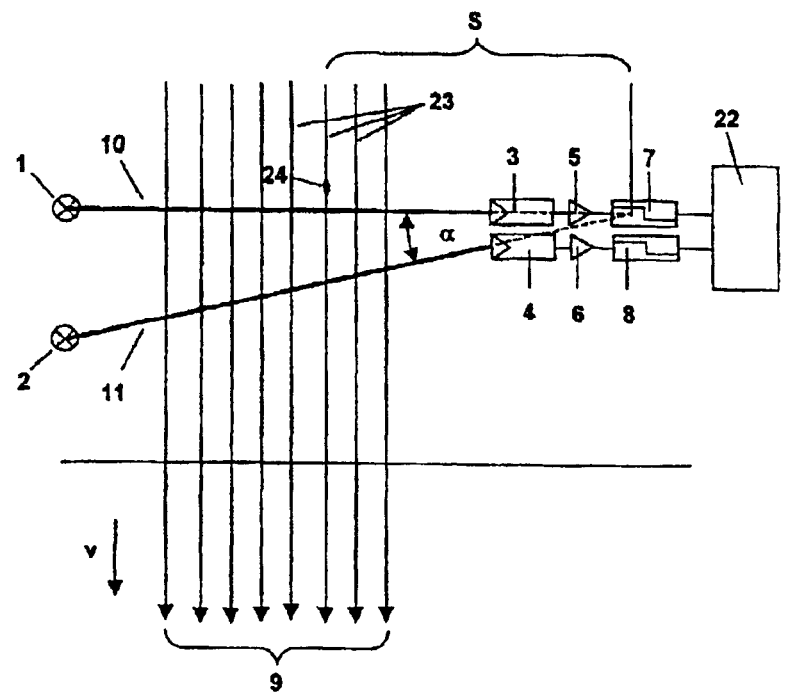
FIG. 3 shows a schematic top view of a yarn sheet and of a V-shaped arrangement of two light barriers whose light beams converge from the light sources, the light beam of one of the light barriers being oriented normal to the yarn traveling direction.
Figure 4:
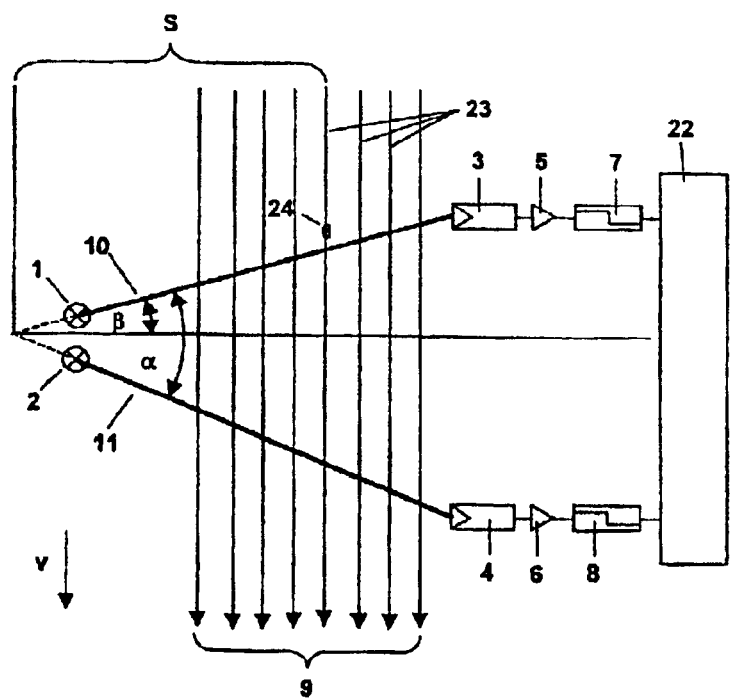
FIG. 4 shows a schematic top view of a yarn sheet and of a V-shaped arrangement of two light barriers whose light beams diverge from the light sources, plus evaluating means for the detector pulses triggered by yarn defects.

An apparatus comprises at least two light barriers 10, 11 whose light beams, as shown in FIGS. 3 and 4 for example, extend in a V-shape relative to each other, each or every light barrier 10, 11 comprising a light source 1, 2 and a detector or photoreceptor 3, 4. In the apparatus of FIG. 3, the light beams of the light barriers 10, 11 converge from the light sources 1, 2 in the direction of a yarn sheet 9. The light barriers 10, 11 are disposed at a suitable distance at right angles to the traveling direction and parallel above or below the plane of the yarn sheet 9 to be monitored. The distance from the yarn sheet 9 to be monitored is in the range from 0.5 to 10 mm. The light barriers 10, 11 are oriented relative to each other in such a way that a yarn defect 24 will travel different distances between the light barriers 10, 11 depending on its position at right angles to the traveling direction of the yarn sheet 9. In the yarn sheet 9, all the ends or yarns 23 have the same traveling velocity v. The different distances covered by the defect on two individual ends from light barrier to light barrier give rise to different times between the two light barriers 10, 11 responding to the passage of the two yarn defects. It is consequently possible to determine the position at right angles to the yarn sheet of the particular end which has a defect on the basis of the difference in these times. Considering an individual end having a defect, the geometry of the light barrier arrangement will result in a certain time difference between the responses of the first and second light barriers on passage of the yarn defect. This time difference is a measure of the position of the yarn defect at right angles to the traveling direction of the yarn sheet 9. In the apparatus of FIG. 3, the V-shaped arrangement of the two light barriers is chosen so that the light beam of the light barrier 10 is normal to the traveling direction of the yarn sheet 9, while the light barrier 11 forms an angle $\alpha$ with the light barrier 10. The time difference is then given by $$T_{1,2}=S*\tan \alpha/v$$

and hence $$S=v*T_{1,2}/\tan \alpha$$

where $T_{1,2}$=time difference between passages of the yarn defect through the light barriers 10 and 11, S=position of the yarn defect at right angles to the traveling direction of the yarn sheet 9 up to the notional point of intersection of the light beams from the two light barriers 10 and 11, $\alpha$ angle between the light beams of the light barriers 10 and 11, v=velocity of yarn sheet.

As soon as a detector signal occurs at both the light barriers 10, 11 within the maximum possible time difference, which corresponds to the travel time of a yarn defect at maximum distance S (outside end of yarn sheet) ("coincidence time"), meaning that a yarn defect has been detected, the yarn sheet 9 is stopped.

Once a yarn defect 24 has been detected by both the light barriers 10, 11 within the maximum allowed time (coincidence time), the yarn sheet 9 is stopped. Owing to the well-known braking delay until the yarn sheet comes to a stop, the yarn defect can be found from the stopping position at a distance S at right angles to the yarn sheet. It must be borne in mind here that, owing to the limited time resolution of the measuring system, the distance S can only be determined with a locational deviation LA, so that the location of the yarn defect can differ by the amount LA from the position S. As the locational deviation increases, the accuracy of measurement decreases.

For a given time resolution $\Delta T$ of the measuring system (detector system/evaluating means), the arrangement of the light barriers which is described in FIG. 3 will have a locational deviation LA for S as a function of the angle $\alpha$ and of the velocity v of the yarn sheet as $$LA = \pm 0.5 * \Delta T * v / \tan \alpha.$$

A time resolution of $\Delta T \leq 0.5$ ms is technically easy to achieve. For typical production conditions of state of the art warp lines (v≦2000 m/min) and the preferred angle range $10° \leq \alpha \leq 45°$, the resulting locational deviation LA is ≦2.5 cm, as is discernible from FIG. 1, which shows the locational deviation LA as a function of the angle $\alpha$ at a time resolution $\Delta T = 0.5$ ms for various yarn sheet velocities v in the range from 300 to 2000 (m/min).

Figure 1:
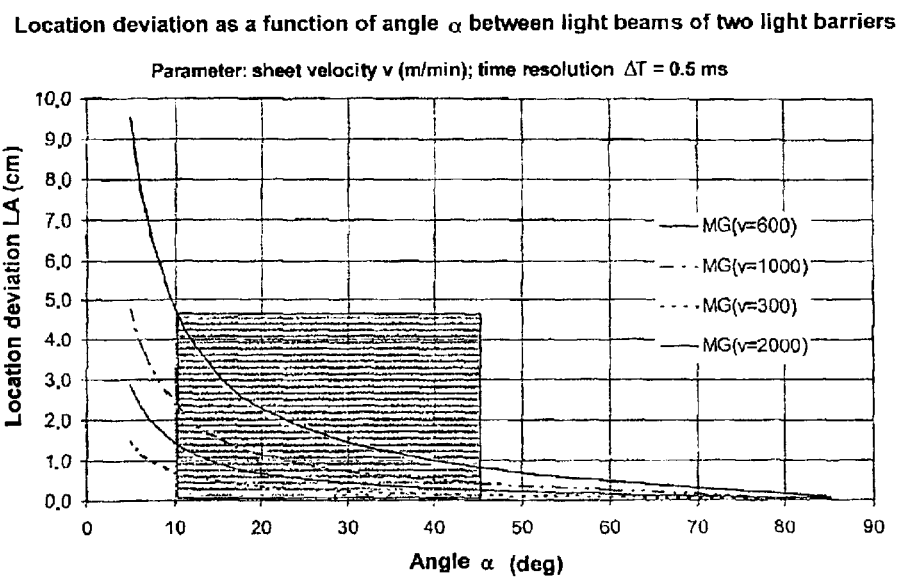
FIG. 1 shows a locational deviation LA of the distance S as a function of an angle $\alpha$ between two light beams of a V-shaped arrangement of two light barriers for a time resolution $\Delta T=0.5$ ms of the measuring arrangement for various traveling velocities v of a yarn sheet.

It can be seen from FIG. 1 that the locational deviation decreases with increasing angle $\alpha$ and increases with increasing velocity v.

This process thus delivers an appreciable time saving to find the yarn defect, since, once the yarn sheet has come to a stop at the stopping position, only a maximum region of 5 cm around the distance S at right angles (perpendicularly) to the yarn traveling direction has to be scoured. By comparison, the operating personnel has hitherto had to scour the yarn sheet over its entire width, which can be 300 cm or more.

FIG. 4 shows another V-shaped arrangement of the light barriers 10 and 11, which diverge from the light sources 1, 2 and form an angle $\alpha$ with each other. The light beam of the light barrier 10 is inclined by the angle $\beta$ against the perpendicular on the traveling direction of the yarn sheet 9, whereas the light beam of the light barrier 11 extends obliquely to the traveling direction of the yarn sheet 9. The light beams emanating from the light sources 1 and 2 are incident upon detectors 3, 4 or photoreceptors whose output signals are conducted to amplifiers 5, 6. The outputs of these amplifiers 5 and 6 are connected to signal-shaping circuits 7, 8 which in turn are connected to evaluating means 22 to determine the time difference $T_{1,2}$ between the two signals which a defect on an individual end will trigger as it passes through the two light barriers 10 and 11. This time difference $T_{1,2}$ constitutes a travel time condition of the yarn defect from a first light barrier to a second light barrier and, given a predetermined velocity v of the yarn sheet 9 and known angles $\alpha$, $\beta$, can be utilized to determine the perpendicular distance S of the yarn defect 24 from the point of intersection of the two light barriers 10, 11.

Figure 5:
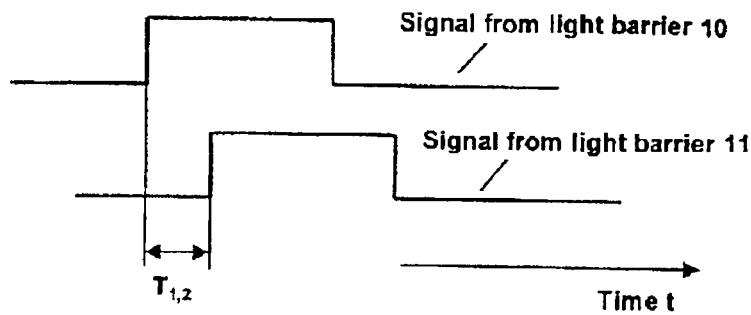
FIG. 5 shows the signal course of a detector pulse triggered by a yarn defect in the two light barriers as per the arrangement according to FIG. 3, FIGS. 6 and 7 show schematic top views of two different arrangements of three light barriers.

FIG. 5 schematically depicts the detector signals from the first light barrier 10 and from the second light barrier 11, which are triggered by the defect 24 on an individual end as it passes through the light barriers, as a function of the time. The time difference $T_{1,2}$ then results from the difference between the front edges of these detector signals on the time axis.

In the more general case of the arrangement of two light barriers in FIG. 4, where the light beams of the two light barriers are inclined relative to the perpendicular on the yarn traveling direction, the travel time of a yarn defect is given by the more general formula $$T_{1,2} = k * S * \tan \alpha / v$$

where the correction factor k $$k = (1 + \tan^2 \beta)/(1 + \tan \alpha * \tan \beta)$$

and the angle $\beta$ describes the inclination of the light beam of the first triggered light barrier against the perpendicular on the yarn traveling direction. When the angle $\beta$ is measured in the clockwise direction with regard to the point of intersection of the two light beams, it has to be negative; when the measurement is in the counterclockwise direction, the angle $\beta$ has to be positive.

Figure 2:
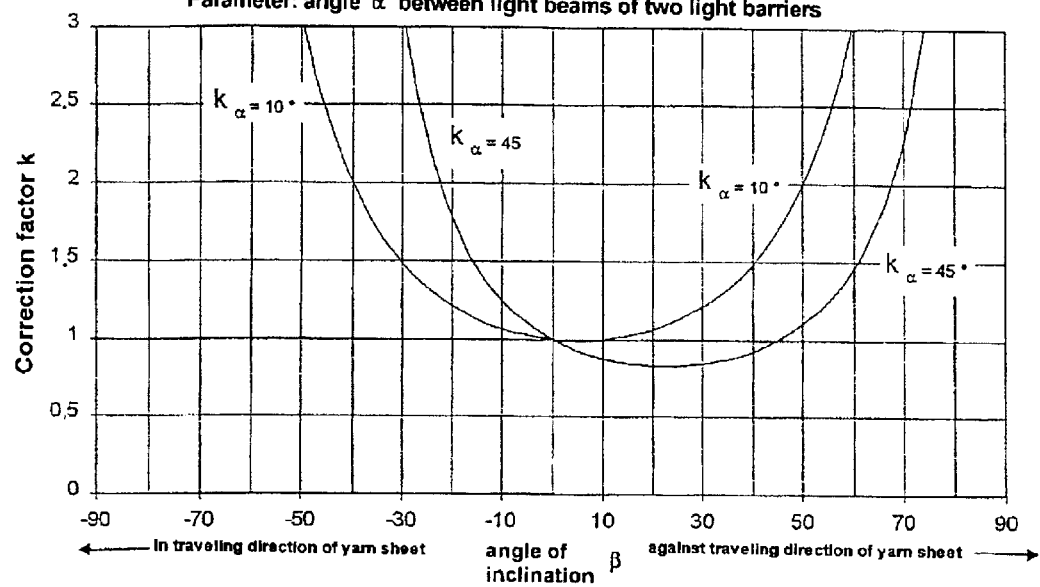
FIG. 2 shows a course of a correction factor k as a function of an angle $\beta$ for the travel time $T_{1,2}$ for a V-shaped arrangement of two light barriers which are both inclined relative to the normal on the yarn traveling direction, the angle $\beta$ representing the inclination of the light beam of the first triggered light barrier relative to the normal.

FIG. 2 shows by way of example values of the correction factor k as a function of the angle of inclination $\beta$ for the preferred range of the intersecting angle $\alpha$ of the light beams. The distance S of the yarn defect at right angles to the yarn traveling direction is then given by $$S = T_{1,2} * v / (k * \tan \alpha)$$

and the locational deviation LA of S for a time resolution $\Delta T$ of the light barrier arrangement is correspondingly given by $$LA = \pm 0.5 * \Delta T * v / (k * \tan \alpha).$$

In the case of a measuring arrangement featuring only two light barriers, as shown in FIGS. 3, 4, the coincidence time, which depends on the geometry of the light barrier arrangement and the velocity of the yarn sheet, cannot be determined automatically, but has to be re-ascertained with every change to the measuring conditions. This can be avoided in the case of arrangements featuring more than two light barriers.

The use of more than two light barriers makes it possible, through the use of conventional coincidence circuits, to check whether the detector signals registered were triggered by one and the same yarn defect and can be assigned to the same individual end. This avoids false stops of the yarn sheet which can be triggered by spurious signals, for example by "jumping" yarn, and ensures that all yarn defects are captured.

As will be more particularly described herein below with reference to FIGS. 6 to 8, the apparatus can also comprise more than two light barriers. The detector in the optical path of an individual light barrier is a photoreceptor for example. The light sources 1, 2 are preferably laser diodes.

To ensure that the evaluated detector signals come from one and the same individual end, the times $T_{i,i+1}$ needed by a yarn defect within the yarn sheet when passing through two adjacent light barriers i and i+1 are determined and compared in the evaluating means. Since, owing to the geometry of the arrangement of the light barriers and the velocity v of the yarn sheet, the time differences $T_{i,i+1}$, i=2, 3, ... n−1 are known as a function of $T_{1,2}$ for each individual end, agreement of a pulse sequence with the expected time differences will show that the evaluated detector signals come from the same yarn defect, i.e. the same individual end, whereas any deviation from the expected time differences will signal that at least one additional spurious signal or a further yarn defect has occurred. When the yarn sheet is brought to a stop, the evaluating means will in this case indicate a multiple defect. The coincidence event leading to the yarn sheet being stopped shall be the detection of at least one yarn defect. Advantageously, the yarn sheet meets an air stream prior to passing through the light barriers and in the region of the light barriers in order that even small yarn defects such as for example broken filaments, which can cling to the yarn, may be blown into the light beams of the light barriers and hence may be more reliably detected.

Figure 6:
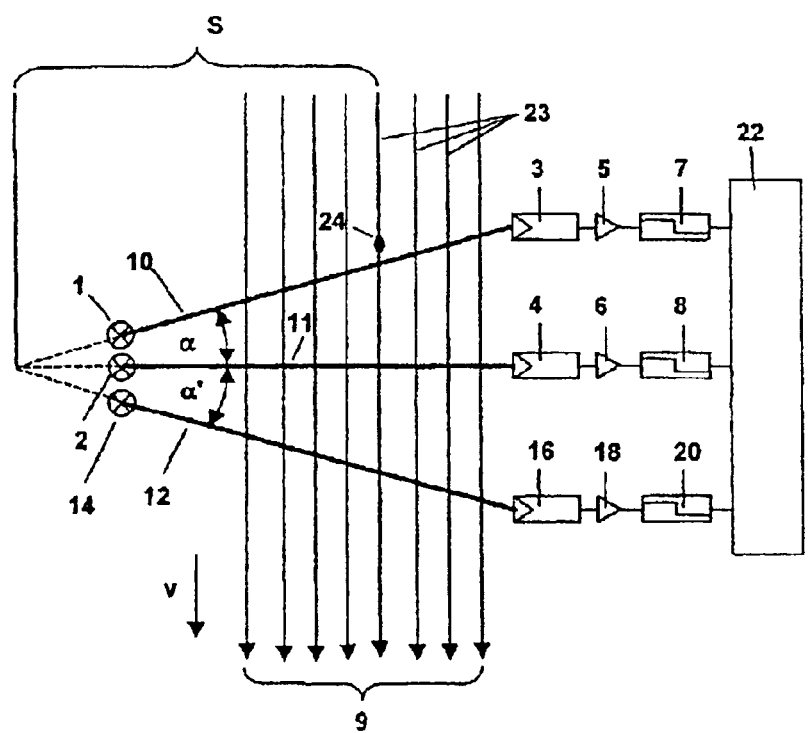
Figure 7:
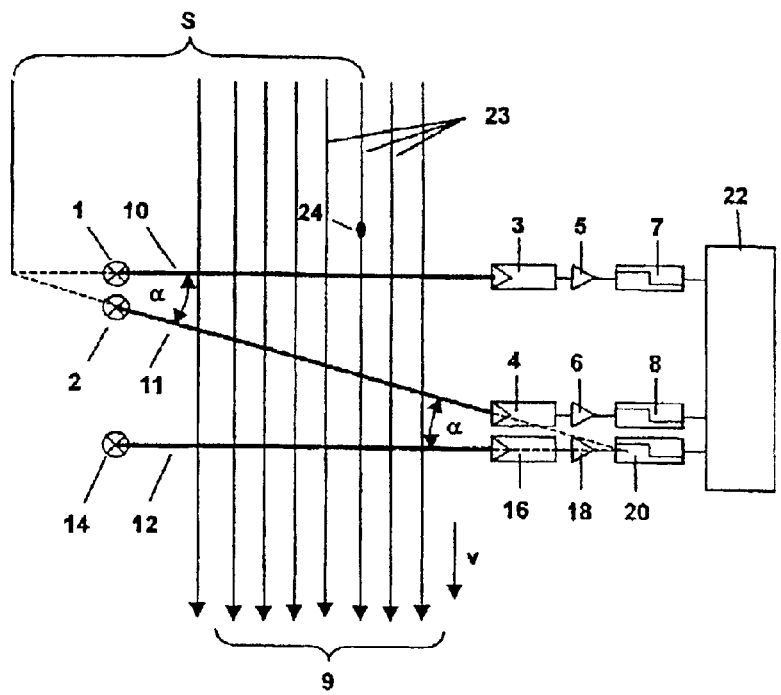

A further embodiment of the apparatus as shown in FIGS. 6 and 7 comprises three light barriers 10, 11 and 12, which are constructed of light sources 1, 2, 14 and detectors 3, 4, 16. The signals of the detectors are supplied to amplifiers 5, 6, 18 which are connected to signal-shaping circuits 7, 8, 20. The outputs of the signal-shaping circuits are fed into the evaluating means 22.

In FIG. 6, the mutually divergent light beams of the three light barriers intersect at a virtual point and the light beam of the light barrier 11 in the middle is disposed perpendicularly to the yarn traveling direction. The angles α and α' are advantageously of the same magnitude. This has the advantage that the travel times of a defect on an individual end between the light barrier pairs 10, 11 and 11, 12 have the same magnitude and it can thereby be checked in a simple manner with substantial reliability whether a yarn defect is present and to which yarn or end it belongs. Here, the coincidence event to stop the yarn sheet is the agreement in the trip times within the two light barrier pairs. A problem arises only when a yarn defect occurs within the dead time of a light barrier immediately after a spurious signal in the measuring arrangement, since the yarn defect will then possibly not be recognized. However, the likelihood of such an event must be deemed extremely small.

The angles α, α' can also be chosen to have different magnitudes, in which case the processing needed to evaluate the detector signals will increase minimally.

FIG. 7 shows an arrangement where the light beams of two light barriers 10 and 12 are oriented perpendicularly to the yarn traveling direction and the light beam of a third light barrier 11 intersects the other two light beams at an angle α at a point outside the yarn sheet. Here, the light barriers 10 and 12 are utilized in a known manner, in a coincidence circuit, for stopping the yarn sheet. The travel time of a yarn defect between one of the two perpendicularly oriented light barriers (10 or 12) and the inclined light barrier 11 defines the position S±LA of the defective yarn in the yarn sheet (at right angles to the traveling direction with regard to the respective point of intersection of the light beams of the chosen pair of light barriers). In this case, the sum total of the travel times $T_{10,11}+T_{11,12}$ can be compared with the travel time $T_{10,12}$ which is constant for all ends to check whether the detector pulses registered by the light barriers can be assigned to a defect on the same individual end.

As well as the arrangements shown here, there are other possible arrangements which meet the same purpose.

By adding a fourth light barrier the assignment of a defect to an individual end can be improved still further and a false event be excluded more reliably, since multiple coincidences can be checked in this case.

Figure 8:
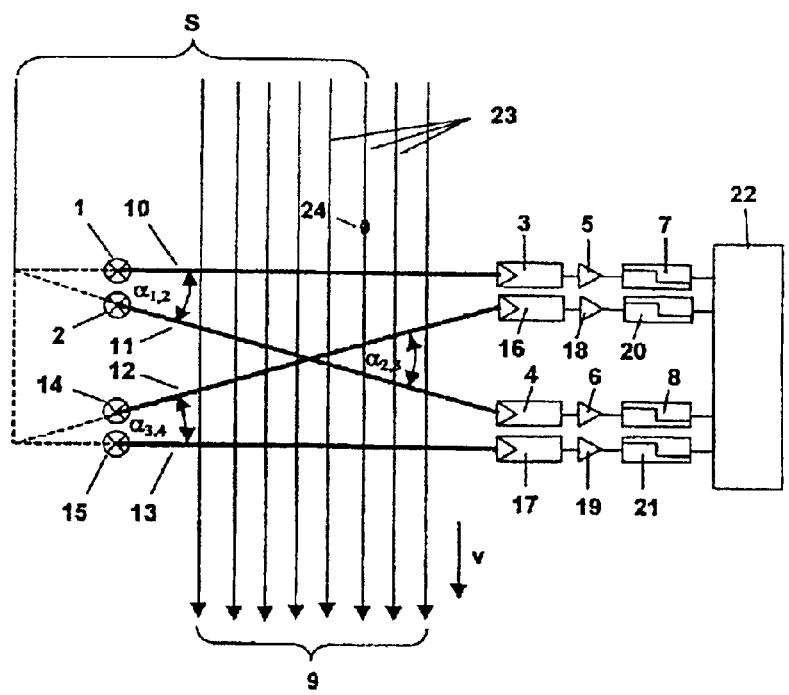
FIG. 8 shows a schematic top view of an arrangement featuring four light barriers.

FIG. 8 shows a schematic illustration of an apparatus featuring four light barriers 10, 11, 12, 13, in which the light beams of the first and second light barriers 10, 11 are at an acute angle $\alpha_{1,2}$ to each other and the third and fourth light barriers 12 and 13 are at an acute angle $\alpha_{3,4}$ to each other. The points of intersection of the light beams of these two light barrier pairs are at the same distance from the yarn sheet. The first light barrier 10 and the fourth light barrier 13 extend perpendicularly to the yarn sheet 9. The angles $\alpha_{1,2}$ and $\alpha_{3,4}$ have the same magnitude, but may also be chosen to have different magnitudes. When the angles $\alpha_{1,2}$ and $\alpha_{3,4}$ have the same magnitude, the travel times of a yarn defect 24 between the first and second light barriers and between the third and fourth light barriers have the same magnitude in each case, which appreciably simplifies the evaluation of the detector signals. Each of the angles $\alpha_{1,2}$ and $\alpha_{3,4}$ is in the range from 5° to 85° and especially in the range from 10 to 45°. Each light barrier 10, 11, 12, 13 comprises a light source 1, 2, 14, 15 and an associated detector or photoreceptor 3, 4, 16, 17. As in the other embodiments of the apparatus, the light sources are preferably laser diodes, but may in some instances also be generated by prismatic beam splitting. The detectors are connected via amplifiers 5, 6, 18 and 19 and signal-shaping circuits 7, 8, 20, 21 to evaluating means 22, in which the travel times of a yarn defect not only between any two adjacent light barriers but also from the light barrier 10 to any of the other light barriers 11, 12, 13 can be determined.

This arrangement combines the advantages of the measuring arrangements shown in FIGS. 6 and 7. The two light barrier pairs 10, 11 and 12, 13 correspond in their function to the two light barrier pairs of FIG. 6 and the light barriers 10 and 13 assume the function of the two outer light barriers in FIG. 7. In addition, the comparison of the sum total of the individual travel times of the yarn defect between the light barrier pairs 10, 11 and 11, 12 and 12, 13 with the total travel time between the two light barriers 10 and 13, which are disposed perpendicularly to the yarn sheet, delivers a further test criterion as to whether the detector pulses registered at the light barriers can be assigned to a defect in one and the same individual end.

Other arrangements of four light barriers which meet the same purpose are likewise possible, as one skilled in the art will immediately recognize. However, the illustrated arrangement has the advantage of a very compact construction.

The yarn sheet 9 comprises in general at least 2 to more than 2000 ends. The light sources 1, 2 of the first and second light barriers 10, 11 and the light sources 14, 15 of the third and fourth light barriers 12 and 13 are disposed side by side in pairs. They can also be replaced, pairwise, by just one single light source whose beam is divided by prismatic beam splitting into two light beams in a conventional manner. The distance between the first detector 3 and third detector 16 and also between the second detector 4 and the fourth detector 17 will only be a few millimeters in a compact construction, these detectors being disposed side by side in pairs. The distance between the two outer light beams is arranged to be not more than 150 cm.

What is claimed is:

1. A process for continuous detection and localization of yarn defects in a yarn sheer which is traveling in a plane and which is scanned by light beams for yarn defects such as protruding filaments, broken filaments, fuzzballs, stripbacks, ringers and the like, each light beam interruption triggered by such a yarn defect triggering a detector signal, which comprises the yarn sheet passing through a measuring arrangement which consists of light barriers made up of light sources and detectors being arranged relative to each other in a V-shape and also evaluating means, the light beams of the light barriers extending parallel to the yarn sheet plane, at constant speed and the travel distances of the individual ends from one light barrier to the adjacent light barrier differing in length, and wherein the detector signal triggered by a defective end within the yarn sheet on passing through the first light barrier is compared with the detector signals of a second and, where appropriate, third and forth light barrier and examined for agreement with or deviations from the travel times of the coincidence conditions concerning the yarn defect to ensure that the evaluated detector signals come from the defect of the same individual end.

2. A process as claimed in claim 1, wherein the light beams of two adjacent light barriers which are disposed in a V-shape either converge or diverge relative to each other from the light sources.

3. A process as claimed in claim 1 or 2, wherein the time difference $T_{1,2}$ between the trip times of a yarn defect through the two light barriers in a V-shaped arrangement of two light barriers in which the light beam of one light barrier is perpendicular to the traveling direction of the yarn sheet is determined as per the equation $$T_{1,2}=S*\tan(\alpha)/v$$

where S is the distance which is perpendicular to the traveling direction of the yarn sheet between the point of intersection of the light beams of the two light barriers and the yarn defect, α is the angle between the light beams of the light barriers and v is the velocity of the yarn sheet.

4. A process as claimed in claim 3, wherein the angle α is in the range from 5° to 85° and especially in the range from 10° to 45°.

5. A process as claimed in claim 3, wherein the velocity v of the yarn sheet is ≦1000 m/min, the angle α is in the range from 10° to 20° and the time resolution ΔT of the measuring arrangement is not more than 0.5 ms, so that the locational deviation LA=±0.5ΔT*v/tan α≦2.5 cm for the position S of a yarn defect.

6. A process as claimed in claim 3, wherein every time difference $T_{1,2}$ is assigned a distance S which indicates a yarn defect in the position S±LA at right angles to the yarn sheet, where LA=0.5*ΔT*v/tan α is the locational deviation and ΔT the time resolution of the measuring arrangement.

7. A process as claimed in claim 1, wherein the time difference $T_{1,2}$ between the trip times of a yarn defect through the two light barriers in a V-shaped arrangement of two adjacent light barriers which are both inclined relative to the normal to the traveling direction of the yarn sheet, the first triggered light barrier including an angle β with the normal that is positive in the counter clockwise direction and negative in the clockwise direction with regard to the point of intersection of the light beams of the two light barriers is determined as per the equation $$T_{1,2}=k*S*\tan \alpha/v \quad (1)$$

where the correction factor $$k=(1+\tan^2 \beta)/(1\pm\tan \alpha*\tan \beta) \quad (2)$$

S is the distance perpendicular to the traveling direction of the yarn sheet between the point of intersection of the light beams of the two light barriers and the yarn defect, α is the angle between the light beams of the light barriers and v is the velocity of the yarn sheet.

8. A process as claimed in claim 7, wherein every time difference $T_{1,2}$ is assigned a distance S as per the equation $$S=T_{1,2}*v/(k*\tan \alpha)$$

which indicates a yarn defect in the position S±LA at right angles to the yarn sheet, with the locational deviation LA conforming to the equation $$LA=\pm 0.5*\Delta T*v/(k*\tan \alpha),$$

where ΔT is the time resolution of the measuring arrangement and is chosen to be not more than 0.5 ms.

9. A process as claimed in claim 1, wherein the travel times of a yarn defect of the individual ends differ from one light barrier to the next light barrier in accordance with the respective position of the individual ends within the yarn sheet.

10. A process as claimed in claim 1, wherein every detector is situated in the optical path of an individual light barrier.

11. A process as claimed in claim 1, wherein the yarn sheet meets an air stream before passing through the light barriers and in the region of the light barriers.

12. A process as claimed in claim 1, wherein the light sources used are laser diodes.

13. A process as claimed in claim 1, wherein the light beams of two or more light barriers are generated by prismatic beam splitting of a single light source.

14. A process as claimed in claim 1, wherein the yarn sheet passes through four light barriers of which the light beams of the two outer light barriers are oriented at right, angles transversely to the yarn sheet and the light beams of the two inner light barriers extend obliquely to the yarn sheet.

15. A process as claimed in claim 14, wherein the yarn sheet which is measured has from 2 to 2000 ends, the light sources of the first and third and of the second and fourth light barrier are disposed pairwise side by side and the distance between the two outer light beams is not more than 150 cm in the yarn direction.

16. A process as claimed in claim 1, wherein the yarn sheet is stopped in the event of a yarn defect occurring, as signaled by at least one detector signal from a light barrier.

17. A process as claimed in claim 1, wherein the yarn sheet is stopped in the event of a yarn defect occurring, as signaled by at least two detector signals from different light barriers that are recorded within a predetermined time window.

18. Apparatus for the continuous detection and localization of yarn defects in a yarn sheet traveling in a plane, comprising light barriers for detecting detector pulses triggered by fuzzballs, broken filaments, protruding filaments, stripbacks, ringers and yarn defects of that kind, wherein at least two light barriers (10, 11) whose light beams form an angle α with each other are disposed at right angles to the traveling direction and immediately above or below the yarn sheet (12) and parallel to the yarn sheet plane and each or every light barrier (10, 11) comprises one of the light sources (1, 2) and a detector (3, 4) plus associated evaluating means, and wherein the detectors (3, 4) are connected via amplifiers (5, 6) and signal-shaping circuits (7, 8) to evaluating means (22) which determines the time difference ($T_{i,i+1}$, where i=1,2,3, ... n−1 from the travel times of a yarn defect from one light barrier (10) to the next light barrier (11), where n is the number of light barriers.

19. Apparatus as claimed in claim 18, wherein the angle α between the light beams of two adjacent light barriers (10, 11) is in the range from 5° to 85°.

20. Apparatus as claimed in claim 19, wherein the angle α between the light beams of two adjacent light barriers (10, 11) is in the range from 10° to 45°.

21. Apparatus as claimed in claim 18, wherein the angle α between the light beams of two adjacent light barriers (10, 11) is in the range from 10° to 45°.

22. Apparatus as claimed in claim 21, wherein the light beam of the middle one of the three light barriers is normal to the yarn traveling direction.

23. Apparatus as claimed in claim 18, wherein there are four light barriers (10, 11, 12, 13), the light beams of the first and second light barriers (10, 11) forming an acute angle α and those of the third and fourth light barriers (12, 13) forming an acute angle α'.

24. Apparatus as claimed in claim 23, wherein the angles α and α' have the same magnitude.

25. Apparatus as claimed in claim 23, wherein the angles α and α' differ in magnitude.

26. Apparatus as claimed in claim 21, wherein the angles α and α' are each in the range from 5° to 85°.

27. Apparatus as claimed in claim 26, wherein the angles α and α' are each in the range from 10° to 45°.

28. Apparatus as claimed in claim 18, wherein each or every light barrier comprises a light source and an associated detector and the detectors are connected via amplifiers and signal-shaping circuits to evaluating means in which the time difference $T_{i,j}$ where i,j=1,2, ... n−1, i≠j are determinable from the travel times of a yarn defect from one light barrier to each or every one of the other light barriers, where n is the number of light barriers.

29. Apparatus as claimed in claim 23, wherein the light sources (1, 2, 14, 15) are laser diodes.

30. Apparatus as claimed in claim 28, wherein the time difference $T_{i,i+1}$ between the trip times of a yarn defect through two adjacent light barriers i and i+1 is predetermined by the yarn velocity v and the geometry of the light barrier arrangement as a function of the distance $S_{i,i+1}$ of the point of intersection of the light beams of these two light barriers to the yarn defect normal to the yarn traveling direction and the angle $\alpha_{i,i+1}$ between the light beams as per the equation $T_{i,i+1} = k_1 * S_{i,i+1} * \tan \alpha_{i,i+1}/v$ where i=1, 2, 3, where $\alpha_{12}$, $\alpha_{23}$ and $\alpha_{34}$ are the angles between a first and second light barrier, between a second and third light barrier and between a third and fourth light barrier and $k_i$ is a correction factor which corrects for the inclination of the i-th light barrier in relation to the normal to the traveling direction of the yarn sheet.

31. Apparatus as claimed in claim 30, wherein the correction factor $k_i = (1 + \tan \beta_i^2)/(1 \pm \tan \alpha_{1,i+1} \tan \beta_i)$ where i=1, 2, 3 includes the angle $\beta_i$ which reflects the inclination of the i-th light barrier in relation to the normal to the traveling direction of the yarn sheet and the (+) sign in the denominator indicates that the adjacent light barriers diverge and the (−) sign indicates that they converge.

* * * * *